United States Patent [19]

Kisilevsky

[11] Patent Number: 6,004,936
[45] Date of Patent: *Dec. 21, 1999

[54] METHOD OF USE OF SERUM AMYLOID A PROTEIN

[75] Inventor: Robert Kisilevsky, Kingston, Canada

[73] Assignee: Queen's University at Kingston, Kingston, Canada

[*] Notice: This patent is subject to a terminal disclaimer.

[21] Appl. No.: 08/458,054

[22] Filed: Jun. 1, 1995

Related U.S. Application Data

[63] Continuation-in-part of application No. 08/203,010, Feb. 28, 1994, abandoned, which is a continuation-in-part of application No. 07/890,936, May 29, 1992, Pat. No. 5,318,958.

[51] Int. Cl.$^6$ .................................................. A61K 38/17
[52] U.S. Cl. ................................... 514/21; 514/2; 514/12
[58] Field of Search ........................................ 514/21, 2, 12

[56] References Cited

U.S. PATENT DOCUMENTS

| | | | |
|---|---|---|---|
| 5,164,295 | 11/1992 | Kisilevsky et al. | 435/7.8 |
| 5,216,127 | 6/1993 | Hirai et al. | 530/380 |
| 5,276,059 | 1/1994 | Caughey et al. | 514/647 |
| 5,318,958 | 6/1994 | Kisilevsky | 514/21 |

FOREIGN PATENT DOCUMENTS

Wo 93 24530  12/1993  WIPO ............................. C07K 15/06

OTHER PUBLICATIONS

Kisilevsky, R., "Serum Amyloid A (SAA) Changes HDL's Cellular Affinity: A Clue to SAA's Principal Function", Annual Meeting Abstracts, Abstract No. 633, p. 107A. (Jan. 1992).

Tape, C., et al.; "Direct Evidence for Circulating apoSAA as the Precursor of Tissue AA Amyloid Deposits", Scand. J. Immunol., vol. 28, pp. 317–324 (1988).

Agnani, G. et al., (1993), "Cholesterol Efflux from Fibroblasts to Discoidal Lipoproteins with Apolipoprotein A–I (LpA–I) Increases with Particle Size but Cholesterol Transfer from LpA–I to Lipoproteins Decreases with Size", Biochem. 32:2643–2649.

Basu, S.K. et al., (1982), "Biochemical and Genetic Studies of the Apoprotein E Secreted by Mouse Macrophages and Human Monocytes", J. Biol. Chem. 257(16):9788–9795.

Brewer et al., (1986) Meth. Enzymol. 128:223–247.

Brissette et al., (1989) "Differential Induction of the Serum Amyloid–A Gene Family . . . ", J. Biol. Chem. 264:19327.

DeLamatre, J., et al., (1986), "Role of apolipoproteins in cellular cholesterol efflux", Biochim. et Biophys. Acta 875:419–428.

Dory, L., (1991), "Regulation of apolipoprotein E secretion by high density lipoprotein$_3$ in mouse macrophages", J. Lipid Res. 32:783–792.

Fidge, N.H. et al., (1985), "Identification of Apolipoproteins Involved in the Interaction of Human High Density Lipoprotein$_3$ with Receptors on Cultured Cells", J. Biol. Chem. 260(6):3750–3575.

Ganapathi, M.K. et al., (1988), "Heterogenous Nature of the Acute Phase Response: Differential Regulation of Human Serum Amyloid A, C–Reactive Protein, and Other Acute Phase Proteins by Cytokines in Hep 3B Cells", J. Immunol. 141(2):564–569.

Glomset, J.A., (1968), "The plasma lecithin: cholesterol acyltransferase reaction", J. Lipid Res. 9:155–167.

Gomori, G. et al., 1942, "A Modification of the Colorimetric Phosphorus Determination for Use with the Photoelectric Colorimeter", J. Lab. Clin. Med. 27:955–960.

Hara, H., et al., (1991), "Interaction of Free Apolipoproteins with Macrophages: Formation of High Density Lipoprotein–Like Lipoproteins and Reduction of Cellular Cholesterol", J. Biol. Chem. 266(5):3080–3086.

Hoffman, J.S. et al., (1982), "Changes in High Density Lipoprotein Content Following Endotoxin Administration in the Mouse: Formation of Serum Amyloid Protein–Rich Subfractions", J. Biol. Chem. 257(17):10510–10517.

Hoffman, J.S. et al., (1982), "Secretion of Serum Amyloid Protein and Assembly of Serum Amyloid Protein–rich High Density Lipoprotein in Primary Mouse Hepatocyte Culture", J. Biol. Chem. 257(17):10518–10522.

Hoffman, J.S. et al., (1984), "Murine Tissue Amyloid Protein AA NH$_2$–Terminal Sequence Identity with Only One of Two Serum Amyloid Protein (ApoSAA) Gene Products", J. Exp. Med. 159:641–646.

Husebekk et al., (1987), "Characterization of Amyloid Proteins AA and SAA . . . " Scand. J. Immunol. 25:375–381.

Jonas, A., (1986), "Reconstitution of High–Density Lipoproteins", Methods In Enzymology 128:553–582.

Kisilevsky, R. (1991), "Serum Amyloid A (SAA), a Protein without a function . . . "Med. Hypotheses 35:337–341.

Kisilevsky, R. et al., (1977), "The Role of Inflammatory Cells in the Pathogenesis of Amyloidosis", Lab. Invest. 37(6):544–553.

Kisilevsky, R. et al., (1992), "Serum Amyloid A Changes High Density Lipoprotein's Cellular Affinity", Lab. Invest. 66(6):778–785.

Liang, J. et al., (1995), "Recombinant human serum amyloid A (apoSAA$_p$) binds cholesterol and modulates cholesterol flux", J. Lipid Res., 36:37–46.

(List continued on next page.)

Primary Examiner—Chhaya D. Sayala
Attorney, Agent, or Firm—Carol Miernicki Steeg; Lahive & Cockfield

[57] ABSTRACT

A method is provided for potentiating the release and collection of cholesterol from inflammatory or atherosclerotic sites in vivo, the method including the steps of increasing the affinity of high-density lipoprotein for macrophages by administering to a patient an effective amount of a composition comprising a compound selected from the group consisting of native serum amyloid A (SAA) and a ligand having SAA properties thereby increasing the affinity of high density lipoprotein (HDL) for macrophages and potentiating release and collection of cholesterol.

10 Claims, 11 Drawing Sheets

OTHER PUBLICATIONS

Lowell, C.A. et al., (1986), "Structure of the Murine Serum Amyloid A Gene Family", *J. Biol. Chem.* 261(19):8442–8452.

Lowry et al., (1951), "Measurement with the Folin Phenol Reagent", *J. Biol. Chem.* 193:265.

Mahley, R.W., (1988), "Apolipoprotein E: Cholesterol Transport Protein with Expanding Role in Cell Biology", *Science* 240:622–630.

Miura et al., (1990), "Intraperitoneal Amylod Formation by Amyloid . . . ", in *Amyloid and Amyloidosis,* p. 523 (Dordrecht, Klumer Academic Publishers).

Narindrasorasak et al., (1991), "High Affinity Interactions between the Alzheimer's . . . ", *J. Biol. Chem.* 266:12878.

Parmelee, D.C. et al. (1982), "Amino Acid Sequence of Amyloid–Related Apoprotein (apoSAA$_1$) from Human High–Density Lipoprotein", *J. Biochem.* 21(14):3298–3302.

Schmitz et al., (1985), "Interaction of High Density Lipoproteins with Cholesteryl Ester Laden Macrophages . . . " *EMBO J.* 4:613–622.

Schumaker et al., (1986) "Sequential Flotation Ultracentrifugation", *Math. Enzymol.* 128:155–170.

Selinger, M.J. et al., (1980), "Monokine–induced synthesis of serum amyloid A protein by hepatocytes", *Nature* 285:498–500.

Steinmetz et al., (1989), "Influence of Serum Amyloid–A on Cholesterol . . . " *Biochem, Biophys. Acta.* 1006:173.

Subrahmanyan et al., (1988), "Effects of Culture Substrates and Normal . . . " *Scand J. Immul.* 27:251.

van der Westhuyzen et al., "Serum Amyloid A Protein Plasma . . . " in *Amyloidosis,* p. 115 (Martinus, Nijhoff, Dordrecht), Section IV, Chapter 3, 1986.

Westermark, G., et al., (1992) "The N–Terminal Segment of Protein AA Determines Its Fibrillogenic Property," *Biochem. and Biophys. Res. Comm.,* 182:1:27–33.

Kisilevsky, R., "Serum Amyloid A Influences The Efflux Of Cholesterol From Macrophages", Amyloid and Amyloidosis 1993, The Proceedings of the VIIth International Symposium on Amyloidosis, Jul. 11–15, 1993, Kingston, Ontario, Canada, pp. 115–118.

METHOD OF USE OF SERUM AMYLOID A PROTEIN

This application is a continuation-in-part of U.S. patent application Ser. No. 08/203,010, filed Feb. 28, 1994, abandoned, which is a continuation-in-part of U.S. patent application Ser. No. 07/890,936 filed May 29, 1992, now U.S. Pat. No. 5,318,958, issued Jun. 7, 1994. The contents of all of the aforementioned applications are expressly incorporated by reference. The contents of all of the referenced published patent applications and issued patents cited throughout this application are expressly incorporated by reference.

TECHNICAL FIELD

The present invention relates to means for potentiating the collection of cholesterol from inflammatory or atherosclerotic sites, having the capability of being used to treat hypercholesterolemia and improving atherosclerotic conditions. More specifically, the present invention provides therapeutic methods which potentiate the ability to transfer macrophage cholesterol to a natural transport mechanism for subsequent excretion.

BACKGROUND OF THE INVENTION

Serum levels of cholesterol and atherosclerosis are significant topics addressed by health care professionals as they relate to cardiac disease, as well as other circulatory and systemic diseases. There is a great interest in the medical field with regard to the reduction of serum cholesterol and the reversal of an atherosclerotic condition.

Various means have been used in an attempt to lower serum cholesterol. For example, various resins have been administered therapeutically to sequester bile acids and thereby reduce systemic cholesterol levels. Other therapeutics have been administered in an attempt to affect cholesterol metabolism. However, there remains a high level of interest and need for more effective therapeutics in this area.

Serum amyloid A (SAA) is an apolipoprotein which is present on high density lipoprotein (HDL) only during inflammatory states. SAA was discovered approximately 15 years ago in the course of studies examining serum for potential precursors to the inflammation-associated AA form of amyloid. It has been determined that the AA peptide responsible for the inflammation-associated amyloid fibril represented a fragment of the SAA protein[12,25]. Based on amino acid sequencing of SAA in the preparation, cloning, and identification of genes possessing the information for this protein[12,20], it became apparent that SAA was not a single protein, but rather a family of several related proteins. Work with these proteins has shown that during an inflammatory reaction, the cytokines interleukin-1, interleukin-6 and tumor necrosis factor are responsible for regulating the transcription of the $SAA_{1+2}$ genes in liver[8,28]. Recent studies have suggested that SAA has a significant influence on lecithin cholesterol acyl transferase activity associated with the HDL.[29]

It is well established that SAA is present in the circulation in substantial quantities only during inflammation. Ninety percent (90%) or more of the SAA is associated with HDL's. HDL is also well established in the function of reverse cholesterol transport[9].

With specific regard to atherosclerosis, observations in the early twentieth century in patients who had long standing infections or malignancies showed that these patients at the time of death had far less atherosclerosis, or had the equivalent of "healed" atherosclerosis, when compared to patients of equivalent age who did not have these preceding disorders. This observation was always attributed to the patient's debilitated physical state or that their nutritional state was inadequate when compared to healthy individuals of the same age.

SUMMARY OF THE INVENTION

Based on the above compiled observations and on studies observing the potential roles of SAA's as a signal to modulate the function of HDL's, the present invention provides means for potentiating the efflux of macrophage cholesterol, thereby providing a means for therapeutically reducing cholesterol at atherosclerotic sites. This potentiating effect leads to reversal of an atherosclerotic condition.

In accordance with one aspect of the present invention, there is provided a method of potentiating the release and collection of cholesterol from inflammatory or atherosclerotic sites in vivo by increasing the affinity of high-density lipoprotein for macrophages, by administering to a patient an effective amount of a composition comprising a compound selected from the group consisting of native serum amyloid A (SAA) and a ligand having SAA properties thereby increasing the affinity of high density lipoprotein (HDL) for macrophages and potentiating release and collection of cholesterol.

In another aspect, the invention features a method of potentiating the release and collection of cholesterol from inflammatory or atherosclerotic sites in vivo comprising: administering to a subject a nucleic acid construct encoding a peptide selected from the group consisting of SAA and a ligand having SAA properties, under conditions such that the construct is incorporated into cells of the subject and the peptide is expressed in the subject, thereby increasing the affinity of high density lipoprotein (HDL) for macrophages and potentiating release and collection of cholesterol.

In yet another aspect, the invention provides a method of reversing an atherosclerotic condition; the method comprises administering to a patient in need thereof an effective amount of a composition comprising a compound selected from the group consisting of native serum amyloid A (SAA) and a ligand having SAA properties, thereby increasing the affinity of high density lipoprotein (HDL) for macrophages and potentiating release and collection of cholesterol, such that an atherosclerotic condition is reversed.

In another aspect, the invention features a pharmaceutical composition, comprising a nucleic acid construct encoding a peptide selected from the group consisting of SAA and a ligand having SAA properties, in a pharmaceutically acceptable carrier.

BRIEF DESCRIPTION OF THE FIGURES

Other advantages of the present invention will be readily appreciated as the same becomes better understood by reference to the following detailed description when considered in connection with the accompanying drawings wherein.

DETAILED DESCRIPTION OF THE INVENTION

Figure 1:
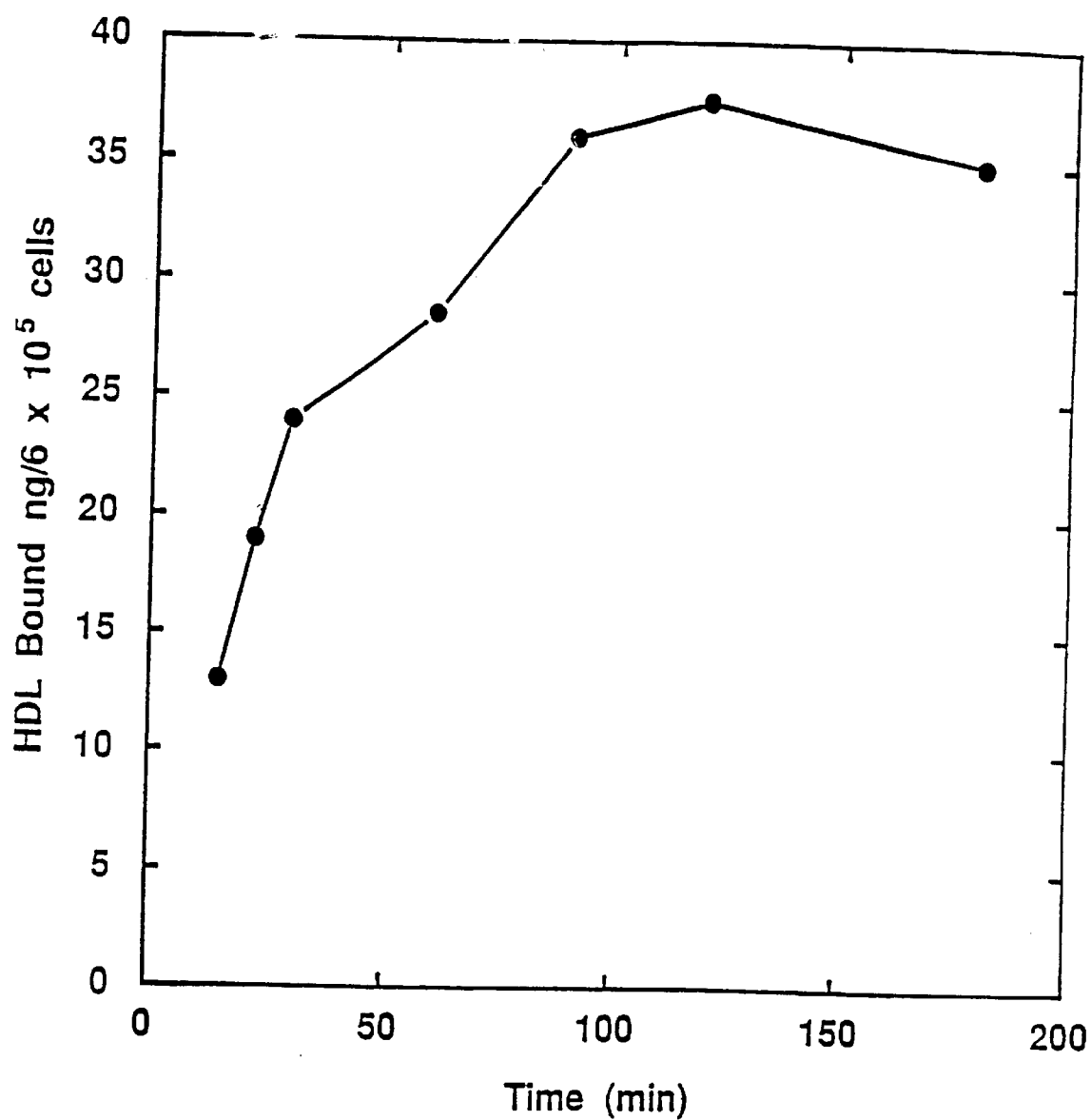
FIG. 1 illustrates a representative binding curve of $^{125}$I-HDL (10 µg/ml) to normal-hepatocytes as a function of time.

Generally, the present invention provides a method of potentiating the collection of macrophage cholesterol by increasing the affinity of high-density lipoprotein for macrophages, exposing the macrophage to HDL, and potentiating the release of macrophage cholesterol to the reverse cholesterol transport mechanism. Although the role of HDL in the physiology of macrophage capacity to carry cholesterol has been studied, the present invention provides the initial discovery of the ability to alter and significantly increase the affinity of HDL for the macrophage using SAA. This increased affinity is biochemically directly related to increased capacity of HDL to collect macrophage cholesterol for subsequent excretion.

More specifically, the affinity of HDL for macrophages is increased by binding serum amyloid-A (SAA) or a ligand having serum SAA binding activity to HDL. This can be accomplished by binding native SAA to HDL or by binding a ligand having SAA affinity binding to the HDL. SAA has been shown to be made by the liver and associates with HDL[13]. However, it has been shown that SAA is secreted from the liver apparently prior to any association with HDL[14]. This indicates that by administering SAA alone, it will associate spontaneously with HDL. Further, SAA has been shown in vitro to spontaneously associate with HDL and displace some HDL-apolipoprotein[31]. Additionally, if a SAA-HDL complex is exposed to apolipoproteins normally found in HDL, the SAA will be replaced by the apolipoproteins[15]. Thus, administration of SAA, in vivo or in vitro, will result in the formation of HDL-SAA complexes as described in detail hereinafter.

It is known that SAA exists in several different native forms, of which some are amyloidogenic, and some are non-amyloidogenic. For example, in the mouse, murine SAA$_1$ and SAA$_2$ are forms of amyloid protein which circulate in the plasma at approximately equal concentrations, but only SAA$_2$ is deposited as amyloid[12,32]. Furthermore, in vitro assays of the fibrillogenic properties of several synthetic peptides corresponding to human and murine protein AA segments have shown that amyloidogenicity of AA proteins may reside primarily in the N-terminal fragment.[33] Thus, when selecting an SAA to administer according to the present invention, it is preferable to select a non-amyloidogenic SAA (or ligand). Such an SAA is preferred since it is possible that administration of an amyloidogenic form of SAA could lead to undesirable amyloid formation as a side effect.

The terms "ligand having serum SAA binding activity to HDL", "ligand having SAA properties" or simply "ligand", as used herein, mean a moiety other than native SAA which is capable of binding to HDL and which is capable of increasing the affinity of HDL for macrophages. A ligand can be derived by isolating the active site of SAA on HDL binding, SAA having been sequenced, cDNA being derived, and the genes being cloned[12,20,25]. Similarly, the active site on SAA for macrophage binding may be determined. Hence, state of the art modeling to derive the active site would result in derivation of a ligand having SAA activity. Ligands useful in the invention may also be identified by testing proposed ligands for the ability to bind to HDL, and the ability to increase the affinity of HDL for macrophages, as described below. The term "SAA/HDL complex", as used herein, refers to a complex formed by the association of SAA or a ligand having SAA properties, as described above, with HDL, either in vivo or in vitro.

As discussed above, preferred ligands will not significantly increase amyloid formation in vivo. Amyloid formation in vivo can be assayed according to the methods described in, for example, R. Kisilevsky et al., (1995) Nature Med. 1:143–148, or U.S. patent application Ser. No. 08/403,230, now U.S. Pat. No. 5,643,562, the contents of both of which are hereby incorporated by reference. Particularly preferred ligands include non-amyloidogenic peptides derived from SAA. Such non-amyloidogenic peptides may be derived from native SAA by cleavage, for example by chemical or enzymatic methods well known in the art, or by other modifications, for example, alkylation or acylation, which may also be by well-known chemical or enzymatic methods. In addition, a ligand can be obtained by coupling of cleavage fragments obtained from native SAA by any of the methods described hereinbefore. Non-amyloidogenic peptides may also be derived by de novo synthesis, including synthesis by chemical or biochemical methods, and may include natural and non-natural amino acids. Illustratively, ligands may be produced by manipulation of the cDNA coding for SAA by techniques of molecular biology, incorporation of the modified cDNA in an appropriate vector, and expression of the recombinant protein in an appropriate host cell, to produce recombinant SAA proteins which contain more, fewer, or altered amino acid residues. The choice of expression vectors and hosts will be routine for the skilled artisan.

Other preferred ligands include non-amyloidogenic peptides which comprise unnatural amino acids, including amino acids of unnatural configuration. The present invention also encompasses peptidomimetic ligands, including "retro-inverso" peptides (see, e.g., U.S. Pat. No. 4,522,752 to Sisto et al.), "peptoids" (see, e.g., Simon et al., Proc. Natl.

*Acad Sci. USA* (1992) 89:9367), and other peptidomimetics known in the art. The choice of a preferred ligand may be made according to considerations such as pharmacokinetics, pharmacodynamics, solubility, efficacy, ease of synthesis, ease of dosing, and the like.

The use of combinatorial libraries to identify ligands is now well established (see, e.g., M. A. Gallop et al., (1994) *J. Med. Chem.* 37: 1233; and E. M. Gordon et al., (1994) *J. Med Chem.* 37: 1385; and references cited therein). Therefore, non-amyloidogenic ligands having SAA properties can be identified by chemical (e.g., solution or solid-phase) or biochemical (e.g., phage-display) synthesis of combinatorial libraries (e.g., of peptides or peptoids) and screening of the resulting libraries according to known techniques. Thus, many potential ligands can be synthesized and screened in a short period of time, and the most active ligands selected for further testing or use.

Administration of the SAA/HDL complex can be accomplished by various means, such as infusion of a solution including the SAA/HDL complex so as to provide an amount of the complex systemically to effectively induce macrophage cholesterol efflux.

The serum amyloid A or a ligand having SAA properties is administered and dosed in accordance with good medical practice, taking into account the clinical condition of the individual patient, the site and method of administration, scheduling of administration, and other factors known to medical practitioners. The "effective amount" for purposes herein is thus determined by such considerations as are known in the art.

In one method according to the present invention, the serum amyloid A or a ligand having SAA properties can be administered in various ways. They can be administered as the compound or as a pharmaceutically acceptable salt and can be administered alone or in combination with pharmaceutically acceptable carriers. The compounds can be administered orally or parenterally including intravenous, intraperitoneal, intranasal and subcutaneous administration. Implants of the compounds are also useful. The patient being treated is a warm-blooded animal and, in particular, mammals including man.

When administering the SAA or ligands having SAA properties parenterally, the pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including anti-microbial preservatives, antioxidants, chelating agents, and buffers, can be added. Prevention of the action of microorganisms can be ensured by various antibacterial and anti-fungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the SAA or ligands having SAA properties can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as polymer matrices, liposomes, and microspheres. An implant suitable for use in the present invention can take the form of a pellet which slowly dissolves after being implanted or a biocompatible delivery module well known to those skilled in the art. Such well known dosage forms and modules are designed such that the active ingredients are slowly released over a period of several days to several weeks.

Examples of well-known implants and modules useful in the present invention include: U.S. Pat. No. 4,487,603, which discloses an implantable micro-infusion pump for dispensing medication at a controlled rate; U.S. Pat. No. 4.,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are well known to those skilled in the art.

A pharmacological formulation of the SAA or ligands having SAA properties utilized in the present invention can be administered orally to the patient. Conventional methods such as administering the compounds in tablets, suspensions, solutions, emulsions, capsules, powders, syrups and the like are usable. Known techniques which deliver the SAA or ligands having SAA properties orally or intravenously and retain the biological activity are preferred.

In one embodiment, the SAA or ligands having SAA properties can be administered initially by intravenous injection to bring blood levels to a suitable level. The levels are then maintained by an oral dosage form, although other forms of administration, dependent upon the patient's condition and as indicated above, can be used. The quantity of SAA or ligands having SAA properties to be administered will vary for the patient being treated and will vary from about 2 mg/kg of body weight to 100 mg/kg of body weight per day and preferably will be from 2 mg/kg to 20 mg/kg per day.

Preparation of SAA/HDL complexes use standard methodologies[27,30]. Isolation of SAA also uses standard methodologies[12,30].

In another aspect of the present invention, a nucleic acid construct which encodes an SAA protein or a peptide having SAA properties is administered to a subject under conditions under which the construct is incorporated into cells of the subject and the peptide is expressed in the subject. This approach is generally referred to as "gene therapy", and has the advantage of providing a long-term supply of the gene product without need for periodic dosing. Approaches to gene therapy include insertion of the subject nucleic acid construct (the "gene") in viral vectors including recombinant retroviruses, adenovirus, adeno-associated virus, herpes simplex virus-1, or recombinant bacterial or eukaryotic plasmids. Viral vectors can be used to transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo or in vitro. It will be appreciated that because transduction of appropriate target cells represents the critical first step in gene therapy, choice of the particular gene delivery system will depend on such factors as the phenotype of the intended target and the route of administration, e.g. locally or systemically.

A preferred approach for in vivo introduction of nucleic acid encoding one of the subject proteins into a cell is by use of a viral vector containing nucleic acid, e.g. a cDNA, encoding the gene product. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding one of the subject SAA peptides or proteins, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM, which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface ligands to the viral env proteins (Neda et al. (1991) *J Biol Chem* 266:14143–14146). Coupling can be in the form of the chemical cross-linking with a protein or other chemical moiety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the SAA (or SAA ligand) gene of the retroviral vector.

In addition to viral transfer methods, such as those illustrated above, non-viral methods can also be employed to cause expression of a SAA protein or a peptide having SAA properties in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject SAA-gene by the targeted cell. Exemplary gene delivery systems of this type include liposomal derived systems, polylysine conjugates, and artificial viral envelopes.

In a representative embodiment, a gene encoding one of the subject SAA proteins or a peptide having SAA properties can be entrapped in liposomes bearing positive charges on their surface (e.g., lipofectins) and (optionally) which are tagged with antibodies against cell surface antigens of the target tissue (Mizuno et al. (1992) *No Shinkei Geka* 20:547–551; PCT publication WO91/06309; Japanese patent application 1047381; and European patent publication EP-A-43075). For example, lipofection of neuroglioma cells can be carried out using liposomes tagged with monoclonal antibodies against glioma-associated antigen (Mizuno et al. (1992) *Neurol. Med. Chir.* 32:873–876).

In yet another illustrative embodiment, the gene delivery system comprises an antibody or cell surface ligand which is cross-linked with a gene binding agent such as polylysine (see, for example, PCT publications WO93/04701, WO92/22635, WO92/20316, WO92/19749, and WO92/06180). For example, the subject SAA-gene construct can be used to transfect hepatocytic cells in vivo using a soluble polynucleotide carrier comprising an asialoglycoprotein conjugated to a polycation, e.g. poly-lysine (see U.S. Pat. No. 5,166,320). It will also be appreciated that effective delivery of the subject nucleic acid constructs via endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al. (1993) Science 260–926; Wagner et al. (1992) PNAS 89:7934; and Christiano et al. (1993) PNAS 90:2122).

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Patent 5,328,470) or by stereotactic injection (e.g. Chen et al. (1994) PNAS 91: 3054–3057).

Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. Various slow release polymeric devices have been developed and tested in vivo in recent years for the controlled delivery of drugs, including proteinacious biopharmaceuticals, and can be adapted for release of viral particles through the manipulation of the polymer composition and form. A variety of biocompatible polymers (including hydrogels), including both biodegradable and non-degradable polymers, can be used to form an implant for the sustained release of an the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

The following experimental data demonstrate the capacity of HDL/SAA administration to significantly shift the HDL cholesterol carrying capacity towards the macrophage. The data specifically demonstrates the effect of SAA to reduce HDL's affinity for normal hepatocytes by a factor of 2. In contrast, the HDL/SAA complex had a 3-to-4 fold higher affinity then HDL alone. A profound effect on this finding is the further finding that the number of binding sites for HDL/SAA increased on macrophages during inflammation, while decreasing on hepatocytes. The data further provide competition experiments showing that there is a specific SAA binding site on macrophages. Hence, it can be concluded from the factual evidence that SAA provides a specific directionality for HDL towards macrophages, the macrophages thereby having an increased capacity of the reverse cholesterol transport mechanism with which to release cholesterol. The net result is a redistribution or excretion of cholesterol from atherosclerosis sites which can result in a therapeutic effect. Thus, there is a use for such a therapeutic in the treatment of atherosclerosis, and also as an adjunct to other cholesterol lowering therapies. Further, the following experiments provide means for demonstrating the patient's HDL effectiveness as a potentiator in combination with the SAA for potentiating the efflux of macrophage cholesterol to the mechanism which transports cholesterol to its natural site for excretion.

SUPPORTING EXPERIMENTS

The following experiments were designed to test whether SAA bound to HDL altered HDL's affinity for specific cells. Further tests were conducted to determine whether cells collected at different times during an inflammatory reaction in turn change in their interactions with HDL or HDL/SAA. Additional experiments demonstrate that the above differences were occurring predominantly through the effect of the SAA protein of the ligand as opposed to the apoA-1.

Binding studies were conducted between various concentrations of HDL, HDL/SAA, and fixed numbers of normal hepatocytes or peritoneal macrophages. Similar binding studies were also conducted with hepatocytes and macrophages obtained at several time points after the induction of inflammation. Binding curves were constructed between macrophages or hepatocytes in different physiological states and various concentrations of HDL or HDL/SAA.

Competition binding studies were conducted between $^{125}$I-HDL, and unlabelled HDL or HDL/SAA for macrophages, and conversely between $^{125}$I-HDL/SAA and unlabelled HDL or HDL/SAA for macrophages. These experiments determined if apoA-1 (the presumed ligand from macrophages HDL binding sites) or the SAA content of the competitor correlated with the inhibition of binding.

Experiments were conducted to show that SAA does bind preferentially to endogenous HDL in vivo. Finally, experiments were conducted on liposomes having a defined cholesterol composition.

Materials and Methods

Collagenase (Type 1) and fatty acid free bovine serum albumin (BSA) were purchased from Sigma Chemical Company, St. Louis, Mo., and iodine monochloride from Aldrich Chemical Company, Milwaukee, Wisconsin. Dibutyl phthalate (d=1.046) and dinonyl phthalate (d=0.97) were obtained from Fluka Chemical Corporation, New York, N.Y. Nitex nylon membrane filters were purchased from B & SH Thompson Company limited, Ville Mont Royale, Quebec. William's medium and RPMI medium were bought from Gibco Incorporated, Grand Island, N.Y.

Animals

All mice were of the CD/1 strain and six-eight weeks old, purchased from Charles Rivers, Montreal, Quebec. Some animals were treated with a subcutaneous injection of 0.5 ml of 2% $AgNO_3$ to produce a sterile subcutaneous inflammatory reaction as described previously by Kisilevsky et all[9].

Preparation of Cells

Hepatocytes. Hepatocytes were isolated from six-eight week old CD/1 mice by liver perfusion. The cells were collected in William's medium which had been pregassed with 95% $O_2$ and 5% $CO_2$ for 15 minutes, washed twice in William's medium and centrifuged for five minutes at room temperature at 150×g. The cells were resuspended in William's medium containing 5 mM HEPES and 2% BSA, counted, and diluted to a concentration of $6 \times 10^6$ cells/ml. They were kept on ice 0–4° C. for ligand binding studies. Hepatocytes were also collected from mice 24 and 72 hours after subcutaneous injections of $AgNO_3$.

Peritoneal Macrophages

Peritoneal macrophages were collected either from normal mice or mice treated with $AgNO_3$ as described above. The mice were sacrificed by cervical dislocation, the peritoneal cavity filled with 5 ml of cold RPMI 1640 medium containing 0.5% BSA and massaged gently by hand. The peritoneal wash containing macrophages was withdrawn with the same syringe and filtered through a Nitex filter (100 μm) into a 50 ml centrifuge tube kept in an ice bath. Washings from 10–12 mice were collected in each tube, centrifuged twice at 300×g for 10 minutes and resuspended in cold RPMI 1640 containing 5 mM HEPES and 2% BSA. Following a cell count, the concentration was adjusted to the desired cell concentration and the diluted suspension kept cold before use in ligand binding experiments.

Preparation of Lipoproteins

Under anesthesia (sodium nembutal 6 mg/kg), mice were exsanguinated from the retroorbital sinus into a small quantity of EDTA which was used as an anticoagulant. Following centrifugation to remove the cells an HDL fraction was prepared from the EDTA treated plasma of normal mice, and those receiving the $AgNO_3$ 24 hours earlier. These plasma samples were fractionated by floatation in $KBr^{27,30}$. After removing the low density lipoprotein (density 1.006–1.063), HDL and HDL/SAA were collected from the top layers of plasma whose density was adjusted to 1.21 with KBr. The collected lipoprotein was overlaid with KBr (density +1.21) and recentrifuged. The washed sample was dialyzed for 24 hours against EDTA saline (10 mM EDTA). The protein content was determined by the standard Lowry techniques[21].

The apolipoproteins were fractionated on Sephacryl S-200 in 10% formic acid. The apoA-I and SAA peaks were pooled, diluted with three volumes of distilled water, lyophilized, delipidated[3], and stored at −20° until ready for use.

Preparation of Liposomes

Liposomes containing apoA-I or SAA were prepared using egg phosphatidyl-choline (PC) and the sodium cholate dispersal technique[16]. After removing any large aggregates by centrifugation, the liposomes were filtered on a 1.5×50 cm Sepharose C1-4B column. liposomes of uniform size were eluted as a single peak (see FIG. 6), with larger complexes emerging in the void column. Following concentration, the liposomes were dialyzed overnight, at 0–4° C., against RPMI 1640 (Gibco), and the protein and phosphate content of the particles were determined[10,21].

Labelling Procedure

High density lipoprotein was iodinated with $Na^{125}I$ using the iodine monochloride method, and purified by ion exchange chromatography. Iodination was done at pH 10, and greater than 95% of the radioactivity was found to be protein bound. On electrophoresis in 12% polyacrylamide gels containing 0.1% SDS and beta mercaptoethanol, followed by autoradiography, only $^{125}I$-apoA-I and $^{125}I$-apoA-II were detectable in the HDL preparations, while apoA-1, SAA, and apoE were detected in the HDL/SAA preparations. In HDL, more than 95% of the protein was represented by apoA-1, while in the HDL/SAA preparations approximately equal quantities of apoA-I and SAA were detected.

Binding Experiments

All binding experiments were performed at 4° C. Both the cells and ligand were kept on ice for at least 30 minutes prior to the experiment. William's medium containing 5 mM HEPES and 2% BSA were used as the medium both for the cells and ligand dilutions. Appropriate concentrations of labelled ligand (final concentrations 0.1–55 μg/ml) were added to known cell concentrations ($5 \times 10^5$–$1 \times 10^6$ cells/ml) in a polypropylene tube (final volume 0.5 ml) which was then tightly closed and incubated for two hours at 4° C. while constantly being mixed on a rotator. The cells were washed free of unbound label by centrifuging a known volume of cell suspension through a layer of equal volumes of medium and phthalate mixture, in a conical microvial in a microfuge. The supernatant containing the incubation medium and the separating oil were removed by aspiration and the remaining liquid was drained. The tip of the microvial, with the cell pellet, was removed with a razor blade and the radioactive counts determined in a gamma counter (Beckman Gamma 550B) with an appropriate background subtraction.

Quantitative Analysis of Binding Data

The binding data were analyzed as described in detail previously[24]. It was assumed that thermodynamic equilibrium for the formation of a ligand and its binding site, and a polynomial was constructed based on a single class of sites where the experimentally measured quantity Bexp was a function of the concentration of ligand [L].

$$B_{exp} = B_0 + S \times [L] + \frac{B_{max} \times [L]}{[L] + Kd}$$

where $B_0$ is the background in the absence of added ligand;

S is the proportionality constant for nonspecific binding; and $B_{max}$ is the total binding capacity.

Additional terms were added when analyzing the data for two classes binding sites, or exponential terms for cooperative binding.

Accordingly, the $B_{exp}$ vs. [1] were analyzed using an objective non-linear curve fitting program (Sigma Plot 4.0, Jandel Scientific). Representative curves and the values of the parameters are illustrated in FIGS. 2 and 3. FIG. 2 shows saturation binding curves of HDL (panel A) and HDL/SAA (panel B) for hepatocytes from various physiological conditions. Log plots of ligand concentrations have been used to better illustrate binding at low concentrations. The individual points represent the experimental data. The solid lines represent the curves of best fit employing the polynomial for a single class of binding sites described above. The parameters were obtained from the curves of best fit. The insets represent Scatchard plots. Each such experiment was performed in triplicate. The spread of results and their statistical analyses are presented in Table 1.

Panel A: A representative curve of HDL binding to normal hepatocytes

Values of parameters are: $B_0$=3 ng; S=$6.3 \times 10^{-3}$ ml.; $B_{max}$=84.8 ng; Kd=2.19 μg/ml Panel B: A representative curve of HDL/SAA binding to hepatocytes 72 hours after inducing inflammation Values of parameters are: $B_0$=0.1 ng; S=$1.3 \times 10^{-3}$ ml; $B_{max}$=77.2 ng; Kd=1.30 μg/ml FIG. 3 shows saturation binding curves of HDL (panel A) and HDL/SAA (panel B) for peritoneal macrophages from various physiological conditions. The individual points represent the experimental data. The solid lines represent the curves of best fit, which provided the values of the parameters listed below. The insets represent Scatchard plots. Each such experiment was performed in triplicate. The spread of results and their statistical analyses are presented in Table 2.

Panel A: A representative curve of HDL binding to normal macrophages

Values of parameters are: $B_0 3.2 \times 10^{-2}$ ng; $S=0.15 \times 10^{-3}$ ml;

$B_{max}=2.1$ ng; $Kd=1.4$ μg/ml

Panel B: A representative curve of HDL/SAA binding to normal macrophages

Values of parameters are: $B_0=3.4 \times 10^{-9}$ ng; $S=0.08 \times 10^{-3}$ ml;

$B_{max}=0.6$ ng; $Kd=0.37$ μg/ml

More complex binding models gave no better curve fits than a single class of binding sites. Scatchard plots have been inserted for completeness, not for the calculation of the parameters which were obtained from the curves of best fit.

Cholesterol Efflux Experiments

Peritoneal macrophages were collected from normal animals as described previously[18]. After culturing for 24 hours in RPMI 1640 and 10% FCS, the cells were washed three times in fresh RPMI 1640 and loaded with $^3$H-cholesterol as described by Delamatre et al.[5] The labelling medium (RPMI 1640) contained 1% FCS, 2 mg/ml BSA, 6 μg/ml PC, 2.4 μg/ml unesterified cholesterol, 2 μg/ml Sandoz 58035 as an ACAT inhibitor, and 0.5 μCi/ml of $^3$H-cholesterol (NEN-NET139). Incubation proceeded for 24 hours following which the cells were washed three times in fresh RPMI 1640 containing 10% FCS and 2 μg/ml ACAT inhibitor, and incubated for a further 24 hours. The labeled cells were then washed five times in fresh RPMI 1640, after which medium containing 1 mg/ml BSA, 2 μg/ml ACAT inhibitor, and the desired liposomes at different concentrations, were added. Control dishes received either no liposomes or liposomes devoid of apolipoprotein. Aliquots, 0.1 ml, were collected at varying time intervals, and the emergent radioactivity determined by liquid scintillation. Effluxed counts were expressed as a percentage of total counts in each dish.

DISCUSSION OF EXPERIMENTAL DATA

Equilibrium Binding of HDL or HDL/SAA

The binding of the ligands (HDL/SAA) to cells (hepatocytes or macrophages) was initially done as a function of time to determine the time needed for the labelled ligand to reach maximum equilibrium binding. The labelled ligand, at a concentration of 10 μg/ml was added to either macrophages or hepatocytes ($6 \times 10^6$/ml) which had been precooled on ice. The ligand and cell suspension were incubated for three hours, mixing constantly in a rotator. Aliquots of the cell suspension (100 μl) were taken at different time points and the cells and attached ligand pelleted through oil as described above. The amount of ligand bound at each time interval was determined from the radioactive counts and knowledge of the specific activity of ligand. FIG. 1 demonstrates a representative binding curve of 125I-HDL to mouse hepatocytes over a period of three hours. Similar results were obtained for HDL/SAA. These experiments were repeated on at least three occasions using separate preparations of cells and ligand. An equilibrium state of binding was reached within 90 minutes. Peritoneal macrophages gave very similar results. A binding time of two hours was therefore used in all subsequent experiments. Specificity of binding was demonstrated by competition experiments in the presence of a hundred fold excess unlabelled ligand which prevented the binding of its corresponding labelled partner. Competition binding studies between labelled HDL and "cold" HDL/SAA and the converse, were also performed.

Saturation Binding Curves

Figure 2A:
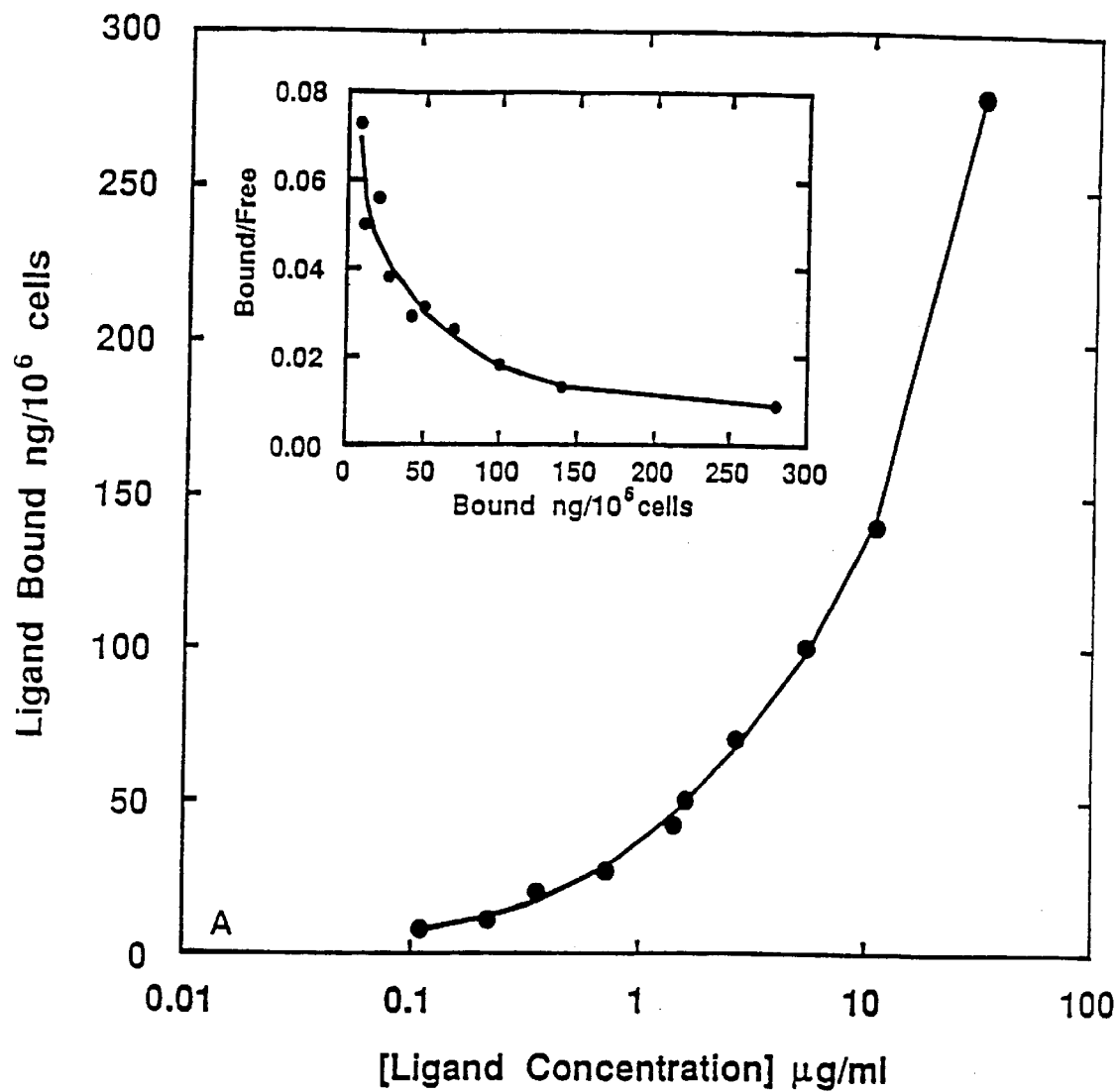
FIG. 2A shows saturation binding curves of HDL for hepatocytes from various physiological conditions.
Figure 2B:
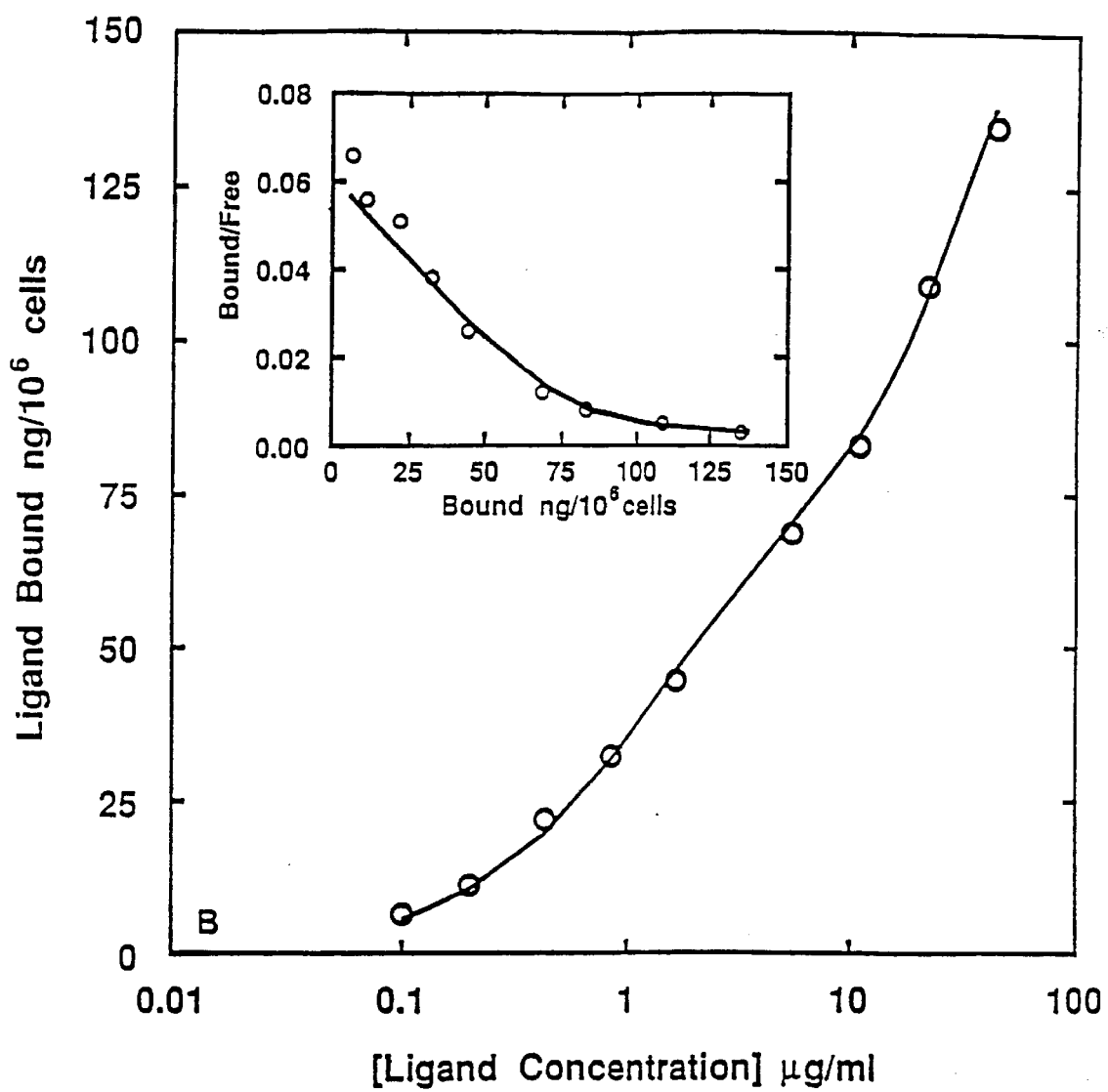
FIG. 2B shows saturation binding curves of HDL/SAA for hepatocytes from various physiological conditions.

Representative examples of saturation binding curves of hepatocytes for varying concentrations of HDL, and for varying concentrations of HDL/SAA are shown in FIGS. 2A and 2B respectively. Scatchard plots of these data are presented as the insets in FIGS. 2A and 2B.

Figure 3A:
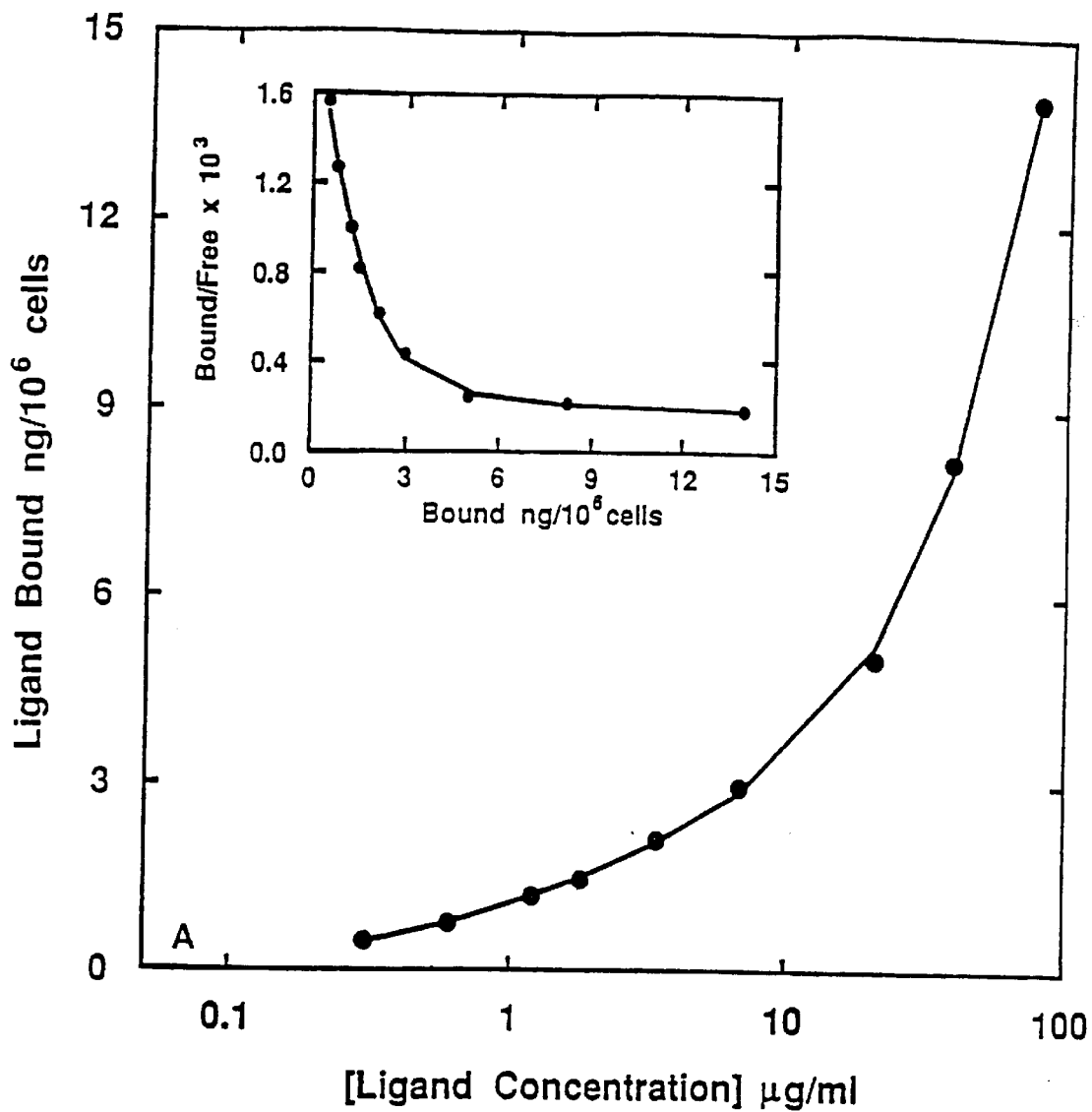
FIG. 3A shows saturating binding curves of HDL for peritoneal macrophages from various physiological conditions, the individual points representing the experimental data and the solid lines representing the curves of best fit, which provided the values of the parameters set forth in the result sections, the insets representing Scatchard plots.
Figure 3B:
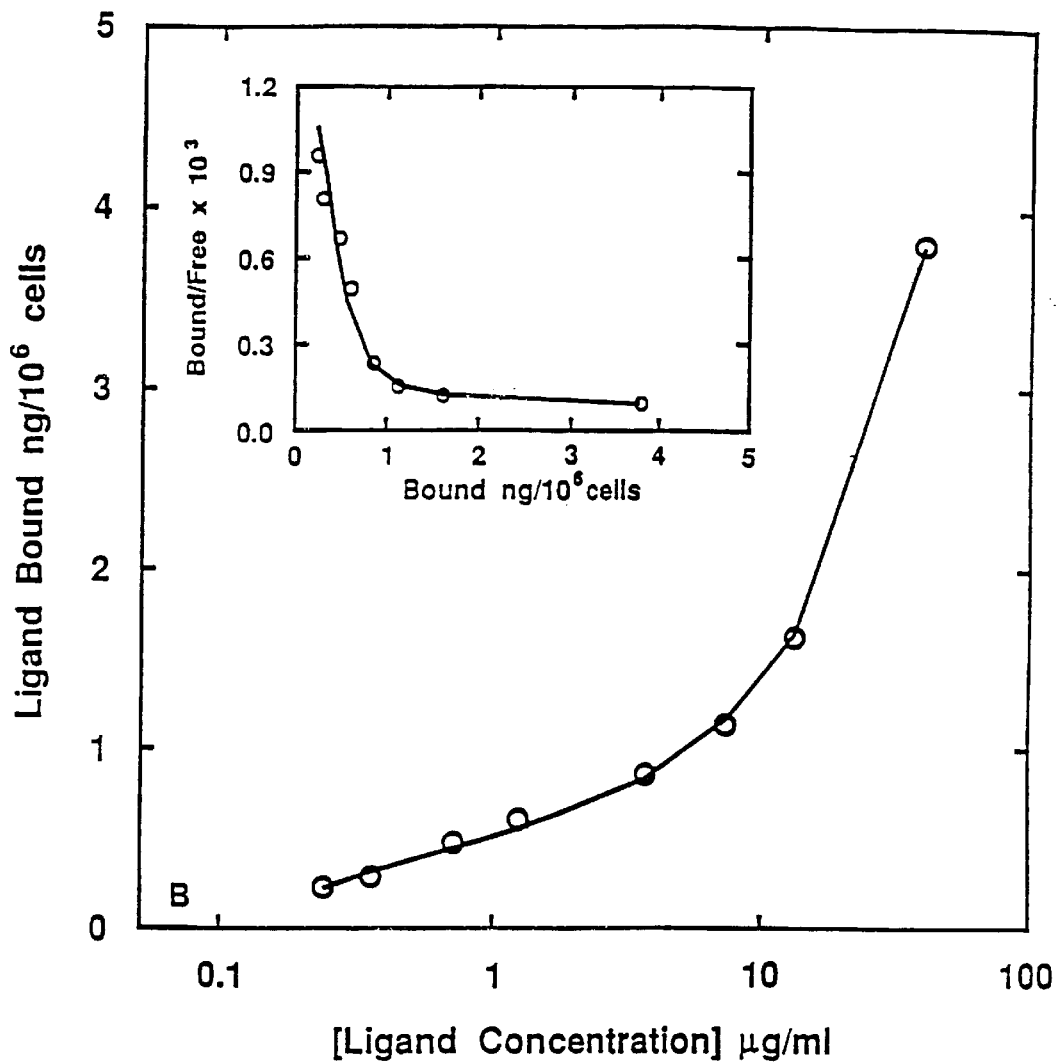
FIG. 3B shows saturating binding curves of HDL/SAA for peritoneal macrophages from various physiological conditions, the individual points representing the experimental data and the solid lines representing the curves of best fit, which provided the values of the parameters set forth in the result sections, the insets representing Scatchard plots.

The individual points in FIG. 2 represent the actual experimental data. The solid lines represent the curve of best fit as obtained from the curve fitting program and the single binding site polynomial described above. Similar binding curves of HDL and HDL/SAA for peritoneal macrophages are shown in FIGS. 3A and 3B respectively.

The dissociation constants (Kd's) and the maximum binding of the ligand ($B_{max}$) were obtained from the best fit parameters, using the aforementioned mathematical formulation as set forth above.

Each of the above experiments were performed in triplicate. A summary and statistical analysis of the Kd's and the $B_{max}$ from the binding studies of HDL and HDL/SAA for hepatocytes from various physiological settings is presented in Table 1. It is apparent that with normal hepatocytes, HDL has an affinity twice as high as HDL/SAA. Twenty-four hours into an inflammatory state, the affinity of HDL for hepatocytes decreased by a factor of 2, but by 72 hours it has returned to a pre-inflammatory level. This result with HDL and hepatocytes probably reflects the large quantity of SAA synthesis and secretion by hepatocytes which occurs in vivo 24 hours following the induction of inflammation[4]. However, it is only the SAA on the surface of the hepatocytes which may complicate the interpretation of the results. Such hepatocyte HDL/SAA on the cell surface may occupy binding sites and allow exogenously added HDL, or HDL/SAA to bind only to unoccupied sites. This would lead to an underestimate of the $B_{max}$ but not alter the Kd's. Any secreted HDL/SAA would compete with exogenous ligand and lead to an underestimate of both parameters. Since all binding studies were done at 0° C., the latter possibility is minimized. These considerations would be less of a problem at the 72 hour interval when HDL/SAA levels drop significantly.

HDL/SAA's affinity for hepatocytes continued to increase with time. The Kd dropped from 32 nM to 17 nM and 6 nM (assuming an average molecular weight of HDL/SAA of 175 kDa) at 24 and 72 hours respectively. A physiologic change is probably taking place in the hepatocyte during inflammation increasing its affinity for HDL/SAA. A potential mechanism involving apolipoprotein E (apoE) is presented below. The hepatocyte $B_{max}$ for HDL did not increase at 24 hours but was two fold higher at 72 hours. In contrast, with HDL/SAA there was relatively little change in $B_{max}$ at 24 hours but a significant drop occurred at 72 hours.

Table 2 contains a summary and statistical analysis of the Kd's and $B_{max}$ for HDL's and HDL/SAA's interaction with peritoneal macrophages. The affinity of HDL/SAA for normal macrophages was three to four fold higher than HDL alone. Twenty-four and 72 hours into an inflammatory reaction, there was no change in HDL's affinity or $B_{max}$ for HDL. Here again there may be an underestimate of the $B_{max}$ at the 24 hour interval as the macrophages are harvested from animals with a high level of SAA. The extent to which endogenous SAA would be a confounding problem in the macrophage binding studies would be far less important than with hepatocytes, since it has been shown that peritoneal macrophages contain little SAA even during inflammation[23]. HDL/SAA consistently had a higher affinity for macrophages than HDL, regardless of time period into the inflammatory reaction at which one examined the macrophages.

It is possible to roughly calculate the number of binding sites per hepatocyte and macrophage from the experimentally determined $B_{max}$ values for $10^6$ cells. Knowing the number of ng of ligand bound per $10^6$ cells, the molecular weights of apoA-1 and SAA and the changing composition of apoA-1 and SAA on HDL 24 hours following the induction of inflammation (from essentially 100% apoA-1, molecular weight 27 kDa to approximately 50% apoA-1, 50% SAA, molecular weight 12 kDa), the HDL binding sites on macrophages remain relatively constant during inflammation at 30,000–35,000/cell. The HDL/SAA binding sites on macrophages increase significantly from 25,000 to 55,000/cell. With hepatocytes the corresponding figures are: for HDL, an increase from 160,000 to 325,000, and for HDL/SAA, a decrease from 400,000 to 95,000. The net effect of both the changes in affinity and numbers of binding sites is a significant shift in HDL cholesterol carrying capacity towards the macrophage.

HDL and HDL/SAA Competition Binding to Normal Macrophages

As demonstrated in the time course experiments, the presence of cold ligand at very high concentration essentially blocked the binding of its radiolabelled counterpart.

Figure 4A:
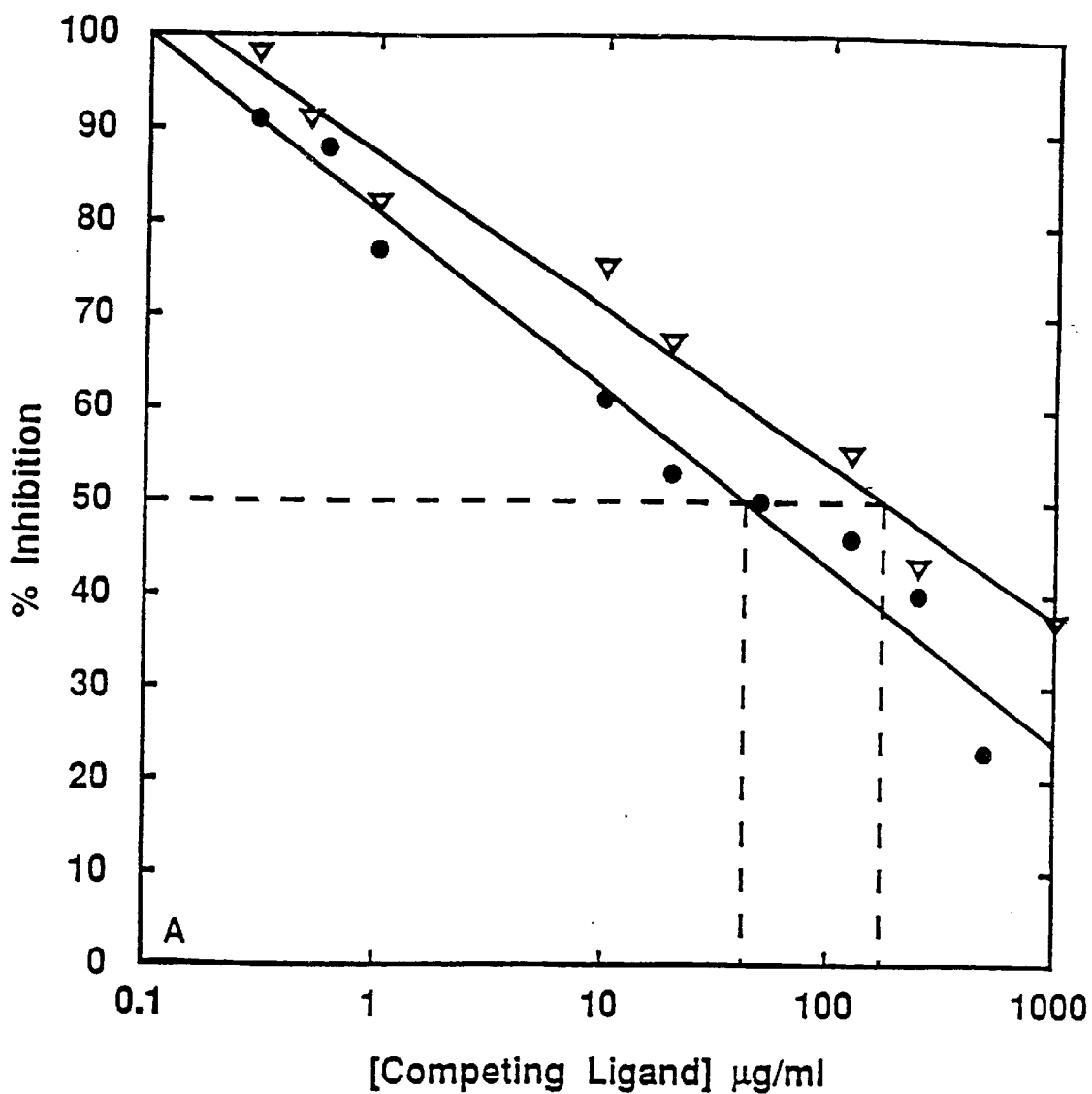
FIG. 4A shows the inhibition of $^{125}$I-HDL binding (10 µg/ml) to macrophages by increasing concentrations of its unlabelled counterpart (filled circles), or unlabelled HDL/SAA (open triangles)
Figure 4B:
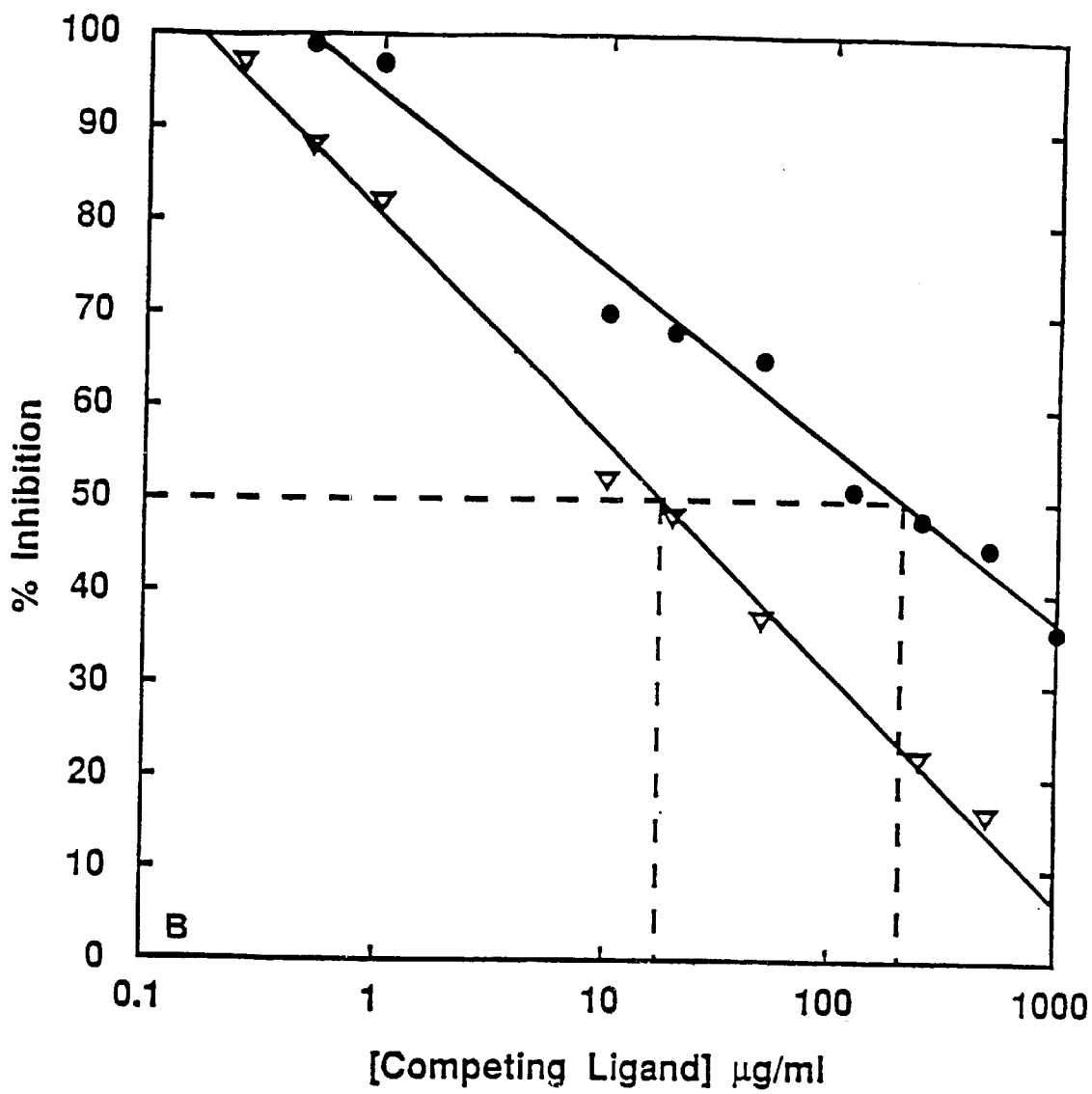
FIG. 4B shows the inhibition of $^{125}$I-HDL binding (10 µg/ml) to macrophages by increasing concentrations of its unlabelled counterpart (open triangles), or unlabelled HDL (filled circles)

To demonstrate both the specificity of binding as well as to examine whether the protein composition of the HDL/SAA or HDL had any influence on the binding of its labelled counterpart, a series of cross incubations were conducted using different concentrations of the unlabelled ligand. The object was to determine the concentration of unlabelled ligand required to produce a 50% reduction in the binding of labelled ligand. These data are shown in FIG. 4 and Table 3.

When using 10 µg/ml of $^{125}$I-HDL, the binding is reduced by approximately 50% with a concentration of approximately 45 µg/ml of "cold" ligand. In contrast, twice as much HDL/SAA is required to achieve an equivalent reduction in the binding of radiolabelled HDL to the same number of macrophages. This is in keeping with the known displacement of approximately half the apoA-1 by an equivalent amount of SAA, and the postulated interaction of HDL and macrophages through an apoA-1 receptor[7,26,31].

When using $^{125}$I-HDL/SAA at 10 µg/ml, approximately 25 µg/ml, unlabelled HDL/SAA were required to reduce the binding of the labelled counterpart by 50%. HDL has a higher apoA-1 content then HDL/SAA. If HDL/SAA was also binding to macrophages solely through apoA-1, then one would expect less unlabelled HDL, than HDL/SAA, to be effective in reducing labelled HDL/SAA binding by 50%. However, HDL was far less effective a competition than HDL/SAA. To achieve a 50% reduction of HDL/SAA binding, approximately 200 µg/ml HDL were required.

These results demonstrate two features. Firstly, the binding of HDL/SAA and HDL to macrophages are specific phenomena. Secondly, the binding of HDL/SAA to macrophages probably occurs through binding sites which do not involve apoA-I.

When placed in the context of HDL function and the process of inflammation our results suggest a novel interpretation of SAA and HDL function in relation to cholesterol metabolism during inflammation.

Figure 5:
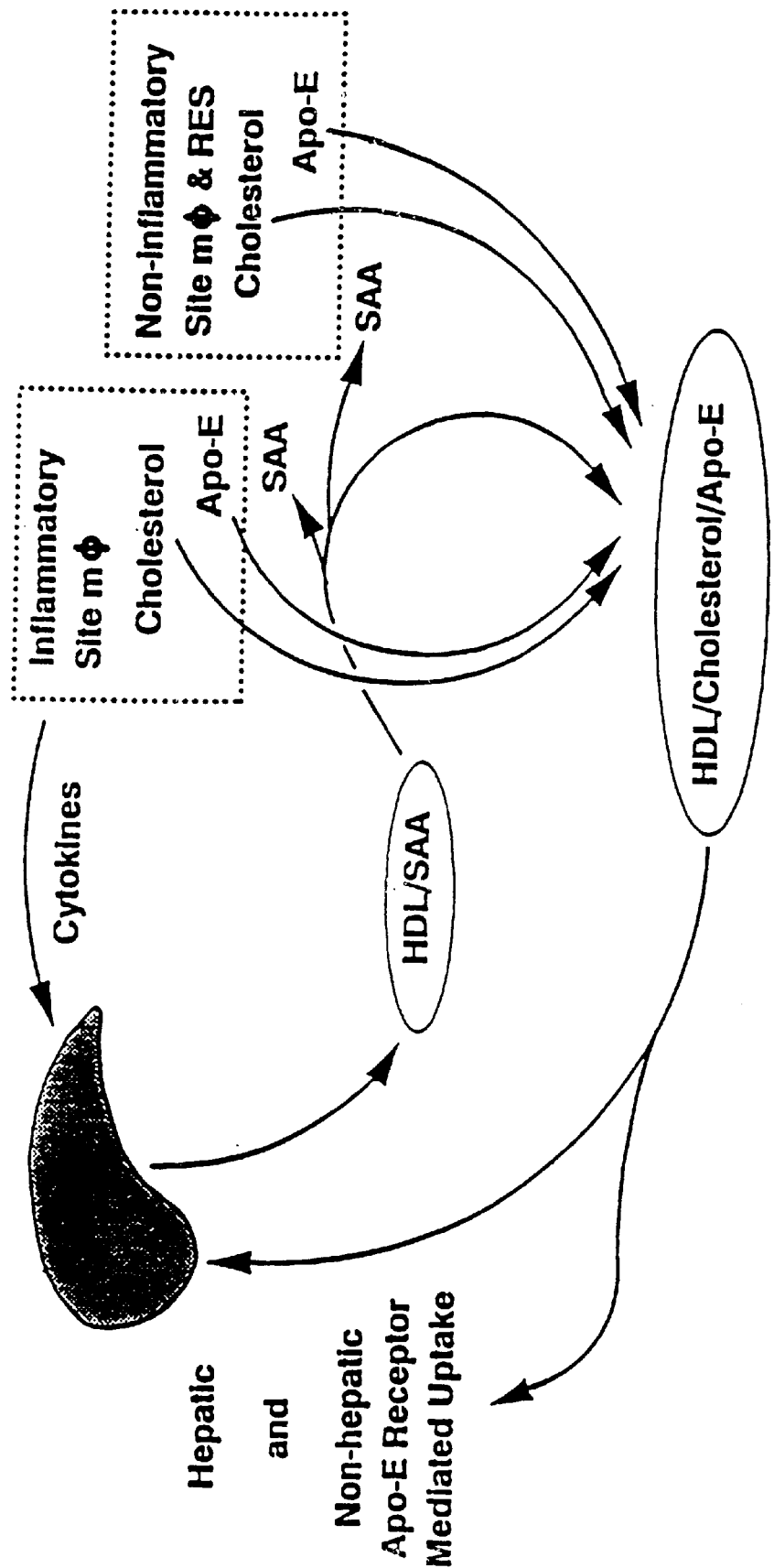
FIG. 5 is a schematic representation of HDL function during inflammatory states.

In an inflammatory reaction cytokines liberated by activated inflammatory cells serve as signals to a variety of cells and organs. In the case of the liver, IL-1, IL-6 and tumor necrosis factor induce the expression of acute phase proteins, among them SAA. SAA in turn associated with HDL as shown herein serves to preferentially direct HDL to macrophages and probably other reticuloendothelial cells (RES). This process would not necessarily depend on the appearance of a new SAA receptor on these cells, although such an event is not excluded. The receptor might already exist on these cells. Its ligand, SAA, would appear only when necessary, addressing HDL to such cells at the time of greatest need, i.e., inflammation. This would be the afferent arm of the reverse cholesterol transport system directing HDL preferentially to those cells which are able to engulf cholesterol and lipid debris, namely macrophage and RES cells. Upon HDL/SAA's interaction with such cells cholesterol efflux and apoE secretion is probably enhanced, a process which has already been demonstrated with macrophages exposed to $HDL_3$, the subfraction to which most of SAA is bound[2,6,11, 22]. The reverse cholesterol transport arm involving apoE described by others[2,22] would now ensure the redistribution of cholesterol or its excretion. During this process, SAA may be displaced and released near RES cells and (if an amyloidogenic SAA) might therefore become available for amyloid formation at these anatomic sites. The entire process is illustrated schematically in FIG. 5. It is one that ensures an efficient and directed lipid/cholesterol transport mechanism during inflammation. Further, from this postulated role emerges the physiologic reason for the specific anatomic localization of inflammation-type amyloidosis.

In response to cytokines released by activated inflammatory cells, SAA is secreted by the liver, and binds to HDL, primarily $HDL_3$. The HDL/SAA particle has a higher affinity for reticuloendothelial cells such as macrophages, than does HDL alone. In addition, macrophages during inflammation develop increased numbers of binding sites for HDL/SAA. Conversely, hepatocytes lose binding sites for HDL/SAA. A net shift of reverse cholesterol carrying capacity towards macrophage-type cells thus occurs during inflammation. On arrival of HDL/SAA, these cells release apoE and cholesterol, a process which likely displaces the SAA. As demonstrated by others, the HDL/apoE/cholesterol complex is transported to sites for receptor mediated uptake/use or excretion.

SAA Binds Preferentially to Endogenous HDL in vivo

Native SAA was labelled with radioactive iodine 125I using a conventional iodine monochloride technique. Aliquots of the labelled SAA were injected intravenously into CD1 mice which, 20 minutes later, were sacrificed and exsanguinated. EDTA was added to the blood as an anticoagulant. Blood from five mice was pooled and, after centrifugation, plasma was collected. Differential centrifugation in potassium bromide at density 1.063 was performed to separate a VLDL and LDL fraction (very low and low density lipoprotein) followed by differential centrifugation in potassium bromide at density 1.21 to separate an HDL fraction. The radioactivity of each fraction was determined: percent of SAA recovered in VLDL/LDL was 7%; in HDL, it was 83.1%; all remaining SAA was 9.9%.

SAA Address Directing HDL to Macrophages During Inflammation

Recent studies have suggested that one function of the acute phase forms of serum amyloid "A" (SAA) may be as an address directing high density lipoproteins (HDL) to macrophages during the process of inflammation[18,17]. The number of SAA binding sites, and potentially the number of SAA receptors, increases on macrophages during the course of inflammation[18]. These observations imply that HDL/SAA particles on reaching cholesterol-laden macrophages should influence the cellular release of cholesterol, perhaps more effectively than HDL alone. Since HDL experiences profound changes in protein[31], and possibly cholesterol and cholesterol-ester, composition during inflammation.

Changes in cholesterol efflux seen with HDL/SAA could be due to the presence of SAA, the loss of other apolipoproteins, or different cholesterol concentration gradients which might exist between the cholesterol-donating cell and the cholesterol-accepting particles. To obviate these problems, a comparison was therefore made between liposomes of defined composition and their efficiency vis a vis macrophages cholesterol efflux.

Figure 6:
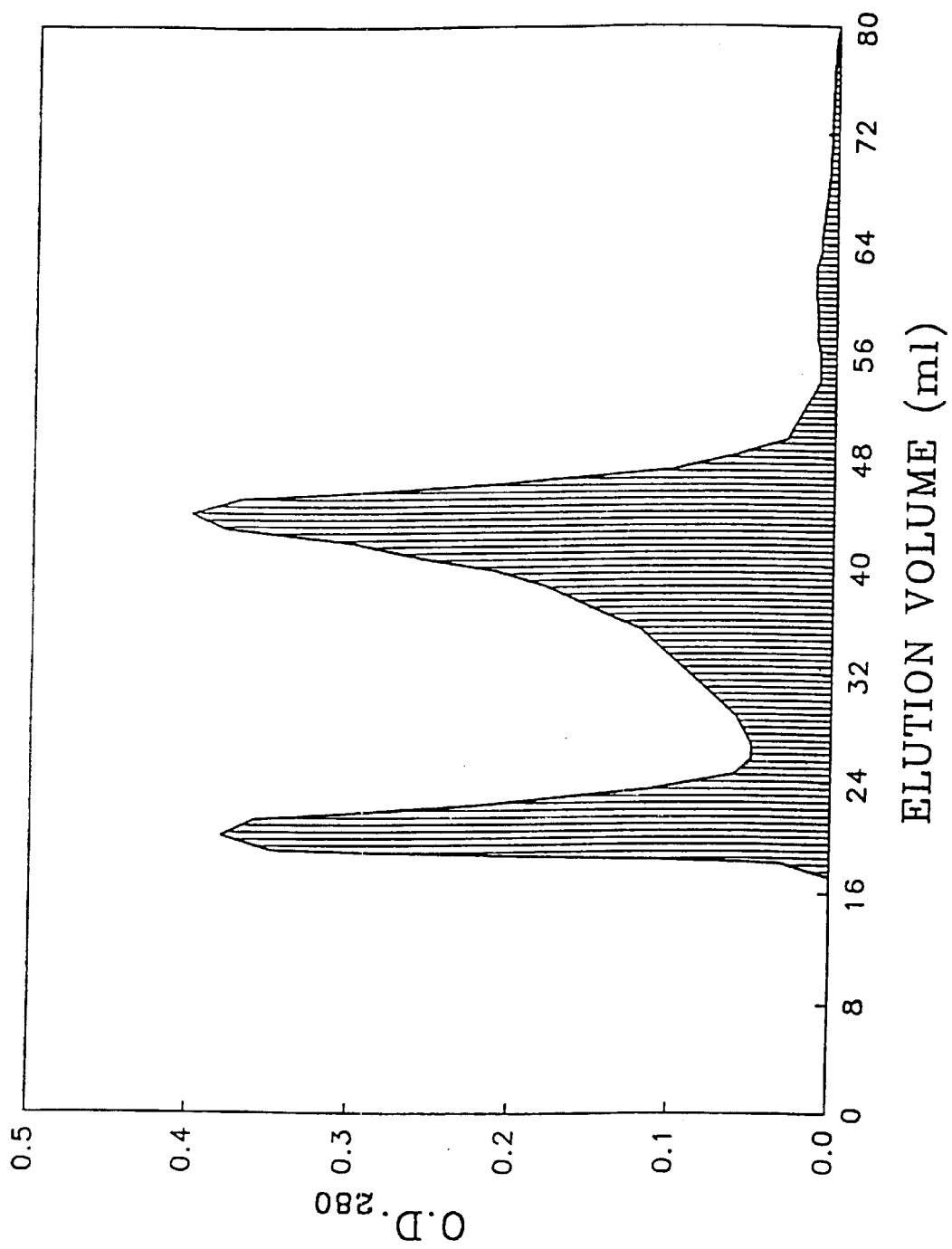
FIG. 6 illustrates the elution profile of apoA-I liposomes (second peak) on Sephacryl S-200; a similar profile was seen with SAA liposomes.

FIG. 6 illustrates the elution profile of apoA-I liposomes (second peak) on Sephacryl S-200. A similar profile was seen with SAA liposomes.

Figure 7:
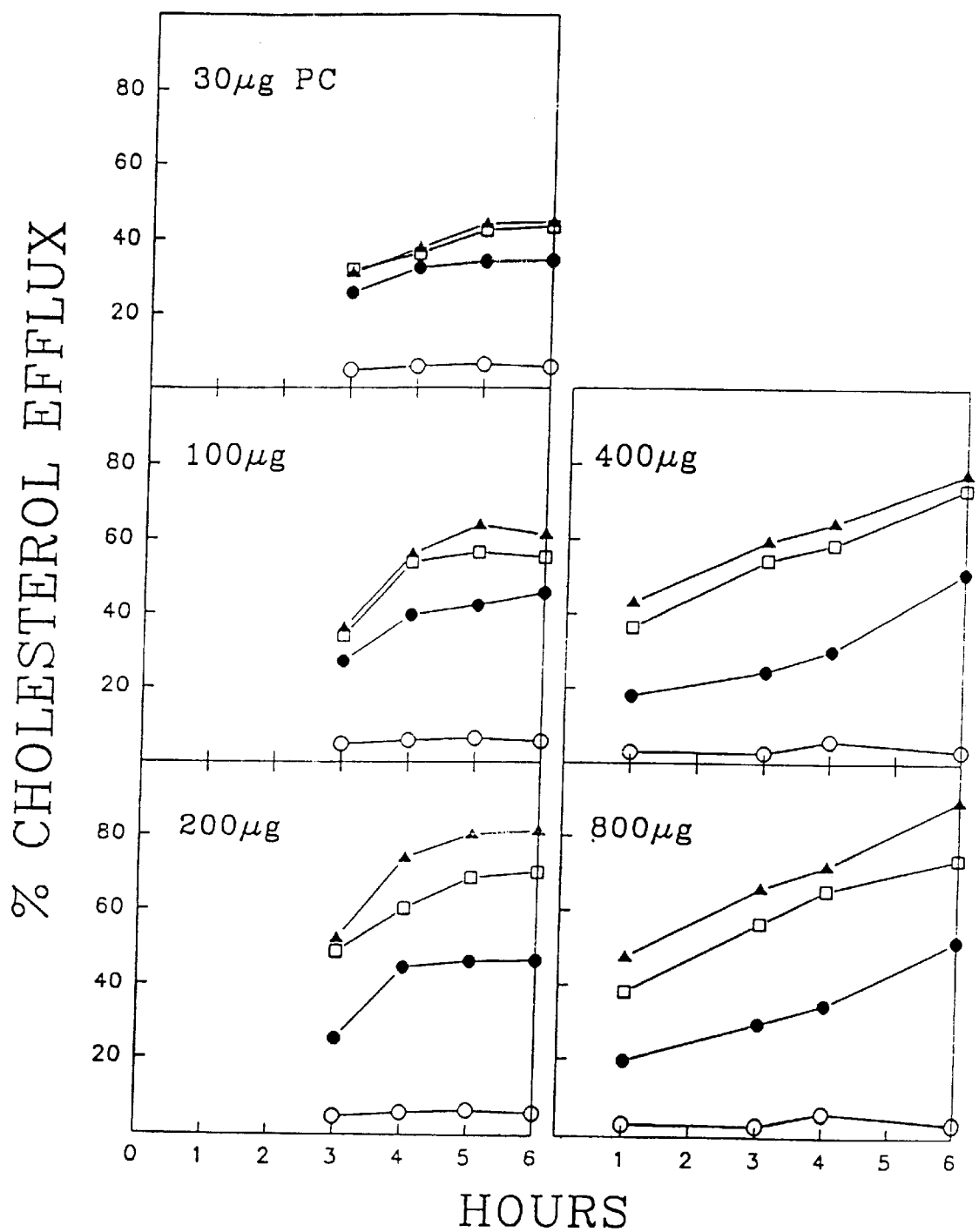
FIG. 7 are graphs demonstrating the effect of different concentrations of liposomes on cholesterol efflux, open circles are controls of medium only, closed circles are liposomes without protein, open squares are liposomes with apoA-I and closed triangles are liposomes with SAA.
Figure 8:
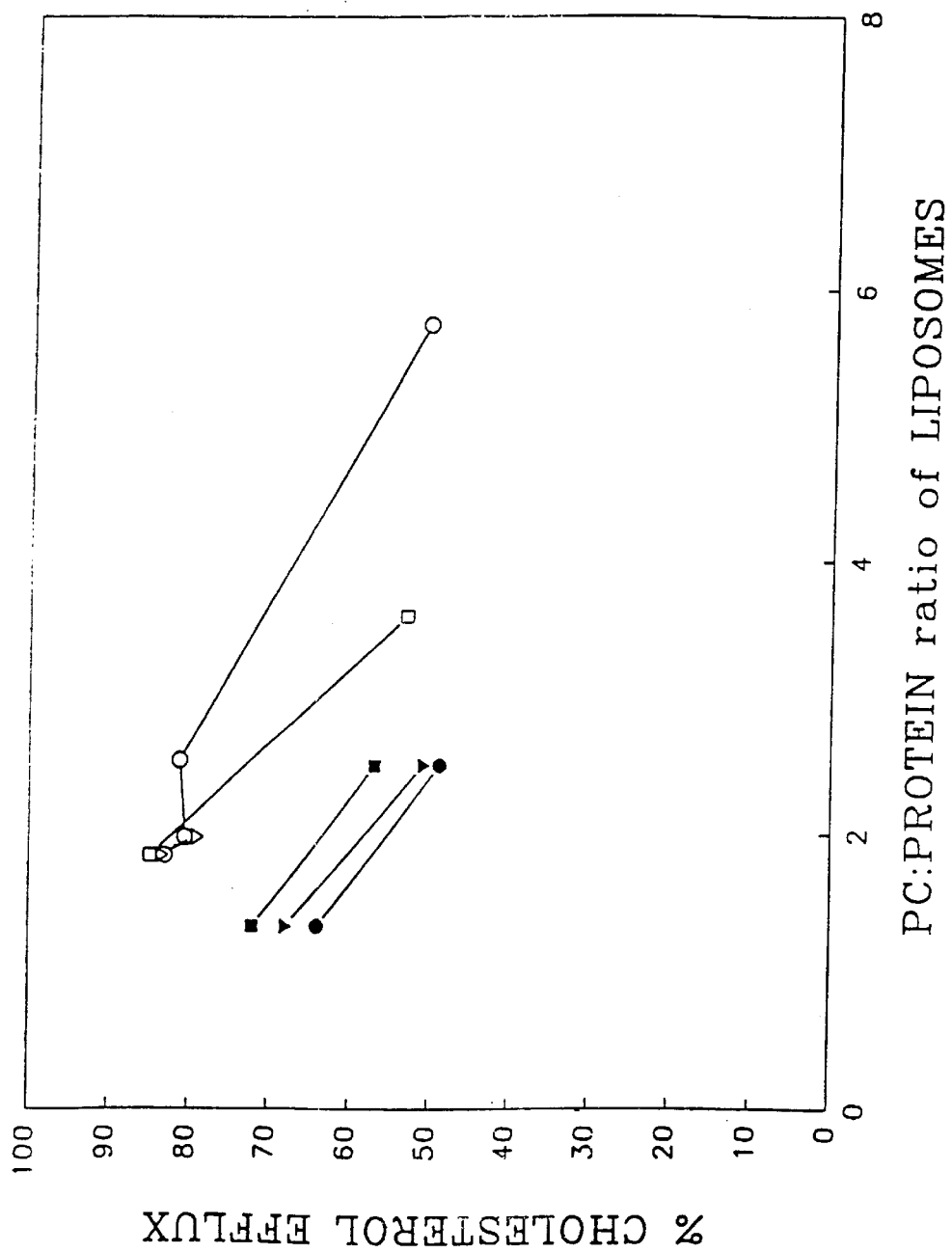
FIG. 8 is a graph of cholesterol efflux as a function of the PC/protein ratio of liposomes, SAA (open symbols), apoA-I (closed symbols), PC at 200 µg/ml (circles), 400 µg/ml (triangles) and 800 µg/ml (squares).

FIG. 7 demonstrates that the rate of efflux was a function not only of the concentration of liposomes, but also the nature of the liposome. In all cases, SAA liposomes were more effective in eliciting cholesterol from macrophages than equivalent concentrations of apoA-I liposomes. Furthermore, as demonstrated in FIG. 8 at equivalent PC/protein ratios, SAA liposomes were consistently more effective as cholesterol acceptors than their apoA-I counterparts.

The present results suggest that SAA in a cholesterol liposome acceptor is more effective at encouraging cholesterol efflux from macrophages than apoA-I. These results are in keeping with the postulated role for SAA as an address to HDL during inflammation directing this reverse cholesterol transporter to macrophages type cells[18]. Though on a molar basis, apoA-I appears to be more efficient than SAA, recent evidence indicates that it is the number of apolipoprotein molecules per HDL particle which is important for both particle stability and cholesterol accepting ability[1].

The above experimental evidence demonstrates the significant shift in HDL cholesterol carrying capacity towards macrophage. Hence, HDL/SAA provide a relevant and significant therapeutic mechanism for removing cholesterol from macrophages at atherosclerotic sites.

The contents of all references and patent applications cited throughout this application are hereby incorporated by reference.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

TABLE 1

SUMMARY OF KDS AND $B_{MAX}$ FROM HEPATOCYTE BINDING STUDIES

| Physiologic setting | $Kd^a$ HDL | $Kd^a$ HDL/SAA | P |
|---|---|---|---|
| Control | 3.18 ± 0.56 | 6.45 ± 0.06 | <0.02 |
| Inflammation 24 hour | 6.53 ± 0.09 | 3.44 ± 0.23 | <0.01 |
| Inflammation 72 hour | 3.61 ± 0.58 | 1.20 ± 0.10 | <0.01 |
| $B_{max}^b$ | | | |
| Control | 80 ± 9 | 203 ± 18 | <0.01 |
| Inflammation 24 hour | 78 ± 14 | 237 ± 74 | <0.05 |
| Inflammation 72 hour | 162 ± 23 | 47 ± 16 | <0.01 |

$^a$Kds are expressed in micrograms/milliliter ± SEM of three experiments.
$^b$$B_{max}$ are expressed as ng/$10^6$ cells ± SEM of three experiments.
Kd values can be converted to M units assuming an average molecular weight for HDL/SAA of 175 kilodalcons.

TABLE 2

SUMMARY OF KDS AND $B_{MAX}$ FROM MACROPHAGE BINDING STUDIES

| Physiologic setting | $Kd^a$ HDL | $Kd^a$ HDL/SAA | P |
|---|---|---|---|
| Control | 2.14 ± 0.75 | 0.54 ± 0.09 | =0.05 |
| Inflammation 24 hour | 2.73 ± 0.50 | 1.26 ± 0.17 | <0.05 |
| Inflammation 72 hour | 2.94 ± 0.58 | 0.45 ± 0.10 | <0.02 |
| $B_{max}^b$ | | | |
| Control | 1.5 ± 0.2 | 0.8 ± 0.1 | <0.01 |
| Inflammation 24 hour | 2.1 ± 0.3 | 1.6 ± 0.1 | $NS^c$ |
| Inflammation 72 hour | 1.7 ± 0.1 | 1.8 ± 0.4 | NS |

$^a$Kds are expressed in micrograms/milliliter ± SEM of three experiments.
$^b$$B_{max}$ are expressed as ng/$10^6$ cells ± SEM of three experiments.
$^c$NS, not significant.
Kd values can be converted to M units assuming an average molecular weight for HDL/SAA of 175 kilodaltons.

TABLE 3

COMPETITIVE BINDING OF HDL AND HDL/SAA FOR MACROPHAGES

| Competitive ligand | Labelled ligand $[^{125}I]$HDL | Labelled ligand $[^{125}I]$HDL/SAA |
|---|---|---|
| HDL | 42.5 ± 2.5 | 215 ± 43* |
| HDL/SAA | 105 ± 15 | 23.5 ± 4.5 |

Values (in micrograms/milliliter) represent the mean of two experiments (except *, mean of three experiments ± SD) and range of values required to reduce labelled ligand binding by 50%. The concentration of labelled ligand in each case was 10 μg/ml.

REFERENCES

1. Agnani and Marcel, 1993, *Biochemistry* 32:2643–2649
2. Basu et al., 1982, "Biochemical and Genetic Studies of the Apoprotein E Secreted by Mouse Macrophages and Human Monocytes", *J. Biol. Chem.* 257:9788
3. Brewer et al., 1986, *Meth. Enzymol.* 128:223–247
4. Brissette et al., 1989, "Differential Induction of the Serum Amyloid-A Gene Family in Response to an Inflammatory Agent and to Amyloid-Enhancing Factor", *J. Biol. Chem.* 264:19327
5. Delamatre et al., 1986, *Biochem. Biophys. Acta* 875:419–428
6. Dory, 1991, "Regulation of Apolipoprotein-E Secretion by High Density lipoprotein in Mouse Macrophages", *J. Lipid. Res.* 32:783
7. Fidge and Nestel, 1985, "Identification of Apolipoproteins Involved in the Interaction of High Density lipoprotein With Receptors on Cultured Cells" *J. Biol. Chem.* 260:3570
8. Ganapathi et al., 1988, "Heterogeneous Nature of the Acute Phase Response: Differential Regulation of Human Serum Amyloid A, C-reactive Protein and Other Acute Phase Proteins by Cytokines in Hep 3B Cells" *J. Immunol.* 141:564
9. Glomset et al., 1968, "The Plasma lecithin: Cholesterol Acyltransferase Reaction", *J. Lipid Res.* 9:155
10. Gomori, 1942, *J. Lab. Clin. Med.* 27:955–960
11. Hara and Yokoyama, 1991, "Interaction of Free Apolipoproteins With Macrophages-Formation of High Density lipoprotein-like lipoproteins and Reduction of Cellular Cholesterol", *J. Biol. Chem.* 266:3080
12. Hoffman et al., 1984, "Murine Tissue Amyloid Protein AA: NH2-Terminal Sequence Identity With Only One of Two Serum Amyloid Protein (ApoSAA) Gene Products", *J. Exp. Med.* 159:641

13. Hoffman and Benditt, 1982a, "Changes in High Density lipoprotein Content Following Endotoxin Administration in the Mouse", *J. Biol. Chem.* 257:10510–10517
14. Hoffman and Benditt, 1982b, "Secretion of Serum Amyloid Protein/Assembly of Serum Amyloid Protein-rich High Density lipoprotein in Primary Mouse Hepatocyte Culture", *J. Biol. Chem.*, 10518–10522
15. Husebekk et al, 1987, "Characterization of Amyloid Proteins AA and SAA as Apolipoproteins of High Density lipoprotein (HDL)", *Scand. J. Immunol.* 25:375–381
16. Jonas, 1986, *Meth. Enzymol.* 128:553–582
17. Kisilevsky, 1991, *Med. Hypotheses,* 35:337–341
18. Kisilevsky and Subrahmanyan, 1992, *Lab. Invest.* 66:778–785
19. Kisilevsky et al., 1977, "The Role of Inflammatory Cells in the Pathogenesis of Amyloidosis", *Lab. Invest.* 37:544
20. Lowell et al., 1986, "Structure of the Murine Serum Amyloid A Gene Family. Gene Conversion", *J. Biol. Chem.* 261:8442
21. Lowry et al., 1951, "Measurement With the Folin Phenol Reagent", *J. Biol. Chem.* 193:265
22. Mahley, 1988, "Apolipoprotein E: Cholesterol Transport Protein With Expanding Role in Cell Biology", *Science* 240:622
23. Miura et al., 1991, "Intraperitoneal Amyloid Formation by Amyloid Enhancing Factor Rich Macrophages in Ascitic Fluid", in: *Amyloid and Amyloidosis* 1990, p. 523. (Dordrecht, Kluwer Academic Publishers)
24. Narindrasorasak et al., 1991, "High Affinity Interactions Between the Alzheimer's beta-Amyloid Precursor Proteins and the Basement Membrane Form of Heparan Sulfate Proteoglycan", *J. Biol. Chem.* 266:12878
25. Parmelee et al., 1982, "Amino Acid Sequence of Amyloid-Related Apoprotein (ApoSAA1) From Human High-Density Lipoprotein", *Biochem.* 21:3298
26. Schmitz et al., 1985, "Interaction of High Density lipoproteins With Cholesterol Ester laden Macrophages: Biochemical and Morphological Characterization of Cell Surface Receptor Binding, Endocytosis, and Resecretion of High Density Lipoproteins by Macrophages", *EMBO J.* 4:613
27. Schumaker and Puppione, 1986, "Sequential Flotation Ultracentrifugation" *Meth. Enzymol.* 128:155
28. Selinger et al., 1980, "Monokine-induced Synthesis of Serum Amyloid A Protein by Hepatocytes", *Nature* 285:498
29. Steinmetz et al., 1989, "Influence of Serum Amyloid-A on Cholesterol Esterification in Human Plasma", *Biochem. Biophys. Acta.* 1006:173
30. Subrahmanyan and Kisilevsky, 1988, "Effects of Culture Substrates and Normal Hepatic Sinusoidal Cells on In vitro Hepatocyte Synthesis of apo-SAA", *Scand. J. Immunol.* 27:251
31. van der Westhuyzen et al., 1986, "Serum Amyloid A Protein in Plasma: Characteristics of Acute Phase HDL", in: *Amyloidosis,* p. 115 (Martinus, Nijhoff, Dordrecht)
32. Shiroo et al., 1987, "Specific Deposition of Serum Amyloid A Protein 2 in the Mouse", *Scand. J. Immunol.* 26:709
33. Westermark, Egstrom, and Westermark, 1992, "The N-terminal Segment of Protein AA Determines Its Fibrillogenic Property", *Biochem. Biophys. Res. Commun.* 182:27

EQUIVALENTS

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method of potentiating the release and collection of cholesterol from inflammatory or atherosclerotic sites in vivo comprising: administering to a patient an effective amount of a composition comprising a compound selected from the group consisting of native serum amyloid A (SAA) and a ligand having SAA properties, wherein said SAA or ligand having SAA properties forms a complex with high density lipoprotein (HDL) and the HDL in said complex has increased affinity for macrophages relative to the affinity of free HDL, thereby potentiating release and collection of cholesterol from inflammatory or atherosclerotic sites.

2. The method of claim 1, wherein the compound is a ligand having SAA properties.

3. The method of claim 2, wherein the ligand is a non-amyloidogenic peptide derived from SAA.

4. The method of claim 1, wherein the native SAA is non-amyloidogenic.

5. The method of claim 1, wherein said HDL/SAA complex binds to a site on the macrophage separate and additional to the binding site for apo A-1 on the macrophage.

6. A method of reversing an atherosclerotic condition, comprising administering to a patient in need thereof an effective amount of a composition comprising a compound selected from the group consisting of native serum amyloid A (SAA) and a ligand having SAA properties, wherein said SAA or ligand having SAA properties forms a complex with high density lipoprotein (HDL) and the HDL in said complex has increased affinity for macrophages relative to the affinity of free HDL, thereby potentiating release and collection of cholesterol, such that an atherosclerotic condition is reversed.

7. The method of claim 6, wherein the compound is a ligand having SAA properties.

8. The method of claim 7, wherein the ligand is a non-amyloidogenic peptide derived from SAA.

9. The method of claim 6, wherein the native SAA is non-amyloidogenic.

10. The method of claim 6, wherein said HDL/SAA complex binds to a site on the macrophage separate and additional to the binding site for apo A-1 on the macrophage.

* * * * *